United States Patent [19]
Ikebe et al.

[11] Patent Number: 4,833,331
[45] Date of Patent: May 23, 1989

[54] METHOD OF HOLDING AN ELECTRICALLY INSULATING SAMPLE

[75] Inventors: Yoshinori Ikebe, Katsuta; Hifumi Tamura, Hachiohji; Eiichi Izumi, Takahagi, all of Japan

[73] Assignee: Hitachi, Ltd., Tokyo, Japan

[21] Appl. No.: 123,114

[22] PCT Filed: Feb. 23, 1987

[86] PCT No.: PCT/JP87/00116
§ 371 Date: Oct. 23, 1987
§ 102(e) Date: Oct. 23, 1987

[30] Foreign Application Priority Data
Feb. 24, 1986 [JP] Japan ................... 61-38550

[51] Int. Cl.$^4$ ............... G01F 21/00; B01D 59/44
[52] U.S. Cl. ................... 250/440.1; 250/282
[58] Field of Search ............... 250/440.1, 282; 427/205, 198

[56] References Cited
U.S. PATENT DOCUMENTS
3,754,976  8/1973  Babecki et al. ............... 427/205
4,719,349  1/1988  Phillips ............... 250/440.1

OTHER PUBLICATIONS
"A Universal Environmental Cell for a 3MV-Class Electron Microscope and its Applications to Metallurgical Subjects", Fujita et al., Jap. Journ. of Applied Physics, vol. 15, No. 11, Nov. 1976, pp. 2221-2228, 250-440.1.

Primary Examiner—Bruce C. Anderson
Attorney, Agent, or Firm—Antonelli, Terry & Wands

[57] ABSTRACT

This invention relates to a method of holding an electrically insulating sample to be bombarded with a corpuscular beam. It is desired that the electrically insulating sample is not charged up when it is placed under the bombardment of the corpuscular beam. To achieve this problem to be solved, an electrically conductive metallic material is placed in a liquefied form on a support member, and the electrically insulating sample is buried in the metallic material except at least the portion that is to be bombarded with the corpuscular beam.

13 Claims, 1 Drawing Sheet

METHOD OF HOLDING AN ELECTRICALLY INSULATING SAMPLE

TECHNICAL FIELD

The present invention relates to a method of holding an electrically insulating sample, and more specifically to a method of holding an electrically insulating sample that is adapted to be used with secondary ion mass spectrometry.

BACKGROUND ART

According to secondary ion mass spectrometry, a sample is bombarded with an ion beam which is a corpuscular beam, and secondary ions emitted from the sample are subjected to mass spectrometry.

The secondary ion mass spectrometry often employs a powdery sample composed of an electrically insulating material. The electrically insulating powdery sample can be held by the following methods:

(1) A method in which one side of a double-sided adhesive tape is stuck to a support member, and the electrically insulating powdery sample is stuck to the other side.

(2) A method in which the sample is dissolved in a solvent which is then applied onto a holder to vaporize the solvent.

According to the method (1) employing the double-sided adhesive tape which is generally an electrically insulating tape, however, the sample bombarded with the corpuscular beam is charged up and the adhesive easily evaporates to contaminate the inner walls of an evacuated sample chamber in which the sample is held as well as the inner walls of the corpuscular beam passage. Therefore, the corpuscular beam impinging upon the sample is undesirably deflected. With the method (2), the sample is prevented from being charged up provided the sample is not too thickly applied onto the holder. However, the sample is degenerated or contaminated with the solvent.

DISCLOSURE OF INVENTION

The object of the present invention is to provide a method of holding an electrically insulating sample which is adapted for preventing the sample from being charged up when it is bombarded with a corpuscular beam.

Another object of the present invention is to provide a method of holding an electrically insulating sample which is adapted for preventing the electrically insulating sample from being charged up when it is bombarded with the corpuscular beam, without relying upon the above-mentioned method (1) or (2).

According to the present invention, there is provided a method of holding an electrically insulating sample to be bombarded with a corpuscular beam comprising the steps of placing an electrically conductive metallic material in a liquefied form on a support member, and burying the electrically insulating sample in the liquefied metallic material except at least a portion to be bombarded with the corpuscular beam.

BRIEF DESCRIPTION OF DRAWINGS

FIG. 1 is a diagram illustrating the steps of a method of holding an electrically insulating sample according to an embodiment of the present invention, wherein:

BEST MODE FOR CARRYING OUT THE INVENTION

Figure 1A:
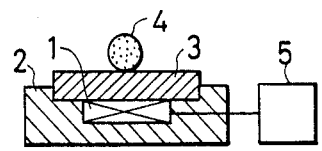
FIG. 1(A) illustrates in cross section the state where an electrically conductive metallic material is placed on a support member that is placed on a base plate.

As shown in FIG. 1(A), a stainless-steel support member 2 is placed on a base plate 2 that is provided with a heater 1, and an electrically conductive metallic material 4 composed of indium (In) having a purity of 99.99% and a melting point of 156° C. is placed on the upper surface of the support member 3. The electrically conductive metallic material 4 may be in the form of a lump or an aggregate of powder or fine pieces.

Figure 1B:
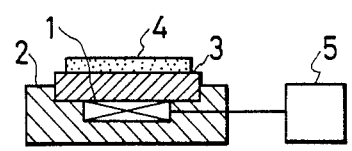
FIG. 1(B) illustrates in cross section the state where the electrically conductive metallic material shown in FIG. 1(A) is flattened.

The heater 1 heats the electrically conductive metallic material 4 via the support member 3, and the heating temperature is changed by adjusting the electric power supplied from a variable heater power source 5 to the heater 1. Under the condition of FIG. 1(A), indium which is the electrically conductive metallic material 4 melts when it is heated by the heater 1 at a temperature higher than its melting point of 156° C., and is transformed into a so-called liquefied metal. This is flattened into a layer having a smooth surface as shown in FIG. 1(B) by using, for example, a flat metal plate.

Then, an electrically insulating powdery sample is sprinkled on the flattened metallic material layer 4, and is nearly uniformly depressed from the upper direction using, for example, a roller or a pressing plate so as to be buried in the metallic material layer 4 but leaving a portion thereof exposed. Thus, the electrically insulating powdery sample is held by the metallic material layer 4.

Thereafter, the metallic material 4 is no more heated by the heater 1, and solidifies after a predetermined period of time has passed. In order to shorten the time required for the solidification, the metallic material 4 may be forcibly cooled.

Figure 1C:
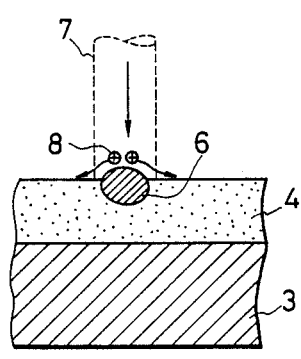
FIG. 1(C) illustrates in cross section the state where an electrically insulating sample is buried in the flattened electrically conductive metallic material shown in FIG. 1(B)

Thus, the electrically insulating sample held by the metallic material 4 is put into use for secondary ion mass spectrometry. That is, the electrically insulating sample held by the metallic material 4 is placed in position in a sample chamber (not shown) of a secondary ion mass spectrometer together with the support member 3, and is placed under the bombardment of an ion beam which is a corpuscular beam, for the purpose of secondary ion mass spectrometry. FIG. 1(C) shows the state where the electrically insulating sample 6 held by the metallic material 4 is placed under the bombardment of an ion beam 7. Here, FIG. 1(C) shows, on a schematically enlarged scale, a grain among a number of electrically insulating powdery grains that form the electrically insulating sample 6. As will be obvious from FIG. 1(C), the ion beam 7 has a size which is greater, in cross section, than the electrically insulating sample 6.

When placed under the bombardment of the ion beam 7, the electrically insulating sample 6 becomes electrically conductive due to the ion bombardment induced conductivity phenomenon. However, the electric charge 8 produced on the surface of the electrically insulating sample 6 is conducted to the electrically conductive metallic material 4. Therefore, the electrically insulating sample 6 is prevented from being charged up, and the ion beam 7 is not desirably deflected by the electrically insulating sample 6 that otherwise is electrically charged up.

Indium which is the electrically conductive metallic material 4 has a high purity and a low vapor pressure, and does not contaminate the samples or the surrounding parts, and does not degenerate the samples, either. The sample can be buried in the metallic material 4 by simply pressing it with a small force; therefore, the sample is not substantially deformed.

In the foregoing embodiment described in conjunction with FIG. 1, the sample was heated by the heater 1. The sample, however, may be heated by radiant heat instead of the heater.

The electrically conductive metallic material 4 for holding the sample may be composed of a material other than indium. When use is made of an electrically conductive metallic material that assumes the liquid state at normal temperature or at temperatures close to normal temperature, such as gallium (Ga) (melting point, 30° C.), mercury (Hg) (melting point, −39° C.), or a like material, there is no need of using the heater 1. The electrically conductive metallic material 4 should desirably be composed of a low-melting metal rather than a high-melting metal from the viewpoint of easiness in burying the sample therein. Examples of the low-melting metal include tin (Sn), bismuth (Bi), lead (Pb) and the like, in addition to the above-mentioned gallium and mercury.

Figure 2:
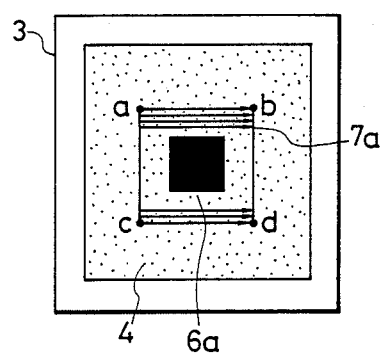
FIG. 2 is a diagram showing part of the steps of the method of holding an electrically insulating sample according to another embodiment of the present invention, and showing in a plan view the state where a pelletized electrically insulating sample is buried in the electrically conductive metallic material that is placed on the support member.

The electrically insulating sample needs not necessarily be of the powdery form but may be of the form of a tiny pellet as designated at 6a in FIG. 2, wherein a region a-b-c-d represents the area scanned by the ion beam 7, and reference numeral 7a denotes scanning lines of the ion beam. It will be obvious that the same effects are exhibited too even in this case.

Figure 3:
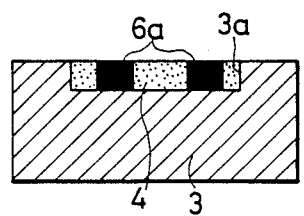
FIG. 3 is a diagram showing part of the steps of the method of holding electrically insulating samples according to a further embodiment of the present invention, and showing in cross sectional view the state where electrically insulating samples are buried in the electrically conductive metallic material in a well that is formed in the support member.

With reference to FIG. 3, the support member 3 is provided with a well 3a, and the electrically conductive metallic material 4 is introduced in the well. If the electrically insulating samples 6a consist of tiny pellets as shown in FIG. 3, the upper surfaces of the samples 6a can be easily brought into flush with the upper surface of the support member 3 using, for example, a pressing plate. Therefore, when the samples are placed in position together with the support member 3 in the sample chamber of the secondary ion mass spectrometer, the position of the samples for the ion beam is automatically determined in the direction of ion beam, obviating the need of adjusting the position every time when the sample is replaced.

Figure 4:
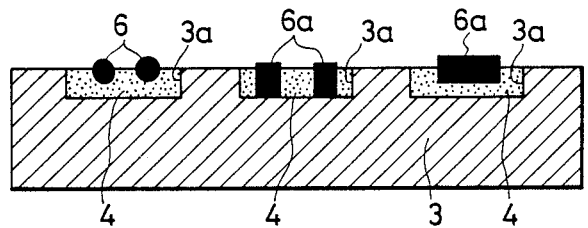
FIG. 4 is a diagram showing part of the steps of the method of holding electrically insulating samples according to a still further embodiment of the present invention, and showing in cross sectional view the state where electrically insulating samples are buried in the electrically conductive metallic material contained in a plurality of wells formed in the support member.

With reference to FIG. 4, the support member 3 is provided with a plurality of wells 3a, 3b and 3c in which is introduced the electrically conductive metallic material. With this setup, many kinds of samples can be placed in position at one time in the sample chamber of the secondary ion mass spectrometer.

It should be noted that the present invention is in no way limited to the above-mentioned embodiments only but can be modified by people skilled in the art in a variety of other ways without departing from the spirit and scope of the present invention.

What is claimed is:

1. A method of holding an electrically insulating sample to be bombarded with a corpuscular beam, comprising the steps of placing an electrically conductive metallic material in a liquefied form on a support member, and burying said electrically insulating sample in the liquefied metallic material except at least a portion to be bombarded with the corpuscular beam.

2. A method of holding an electrically insulating sample to be bombarded with a corpuscular beam, comprising the steps of placing an electrically conductive metallic material in a liquefied form on a support member, pressing the liquefied metallic material onto said support member using a member having a flat surface so as to substantially flatten the surface of said liquefied metallic material, and burying said electrically insulating sample in said liquefied metallic material except at least a portion to be bombarded with said corpuscular beam.

3. A method of holding an electrically insulating sample to be bombarded with a corpuscular beam, comprising the steps of placing an electrically conductive metallic material on a support member, heating the metallic material so as to liquefy the same, and burying said electrically insulating sample in the liquefied metallic material except at least a portion to be bombarded with said corpuscular beam.

4. A method of holding an electrically insulating sample to be bombarded with a corpuscular beam, comprising the steps of placing an electrically conductive metallic material on a support member, heating the metallic material so as to liquefy the same, pressing the liquefied metallic material onto said support member using a member having a flat surface so as to substantially flatten the surface of said liquefied metallic material, and burying said electrically insulating samples in said liquefied metallic material except at least a portion to be bombarded with said corpuscular beam.

5. A method according to claim 3 or 4, which further comprises the step of cooling the electrically conductive metallic material in which said electrically insulating sample is buried so as to solidify the electrically conductive metallic material.

6. A method according to claim 1, 2, 3 or 4, wherein said electrically insulating sample is powdery.

7. A method according to claim 1, 2, 3 or 4, wherein said electrically conductive metallic material is the one that is selected from a group consisting of gallium, mercury and indium.

8. A method according to claim 1, 2, 3 or 4, wherein said electrically insulating sample is powdery, and said electrically conductive metallic material is the one that is selected from a group consisting of gallium, mercury and indium.

9. A method according to claim 1, 2, 3 or 4, wherein said electrically conductive metallic material is one selected from the group consisting of tin, bismuth and lead.

10. A method according to claim 1, 2, 3 or 4, wherein said electrically insulating sample is in the form of a pellet.

11. A method according to claim 1, 2, 3 or 4, wherein said support member has a well portion extending from a surface thereof, and the liquefied metallic material is placed on the support member in the well portion.

12. A method according to claim 1, 2, 3 or 4, wherein the electrically insulating sample is buried in the liquefied metallic material such that the electrically insulating sample is held by the metallic material.

13. A secondary ion mass spectrometry method, comprising the steps of placing an electrically conductive metallic material in a liquefied form on a support member; burying an electrically insulating sample in the liquefied metallic material except at least a portion to be bombarded with an ion beam which is a corpuscular beam; bombarding said sample with said ion beam; and subjecting secondary ions emitted from the bombarded sample to mass spectrometry.

* * * * *